United States Patent [19]

Ohgoshi et al.

[11] Patent Number: 5,321,196
[45] Date of Patent: Jun. 14, 1994

[54] PROCESS FOR ALKYLATING AN ISOPARAFFIN WITH A SALT OF A HETEROPOLY-ACID AS A CATALYST

[75] Inventors: Shingo Ohgoshi; Junichi Kanai; Michio Sugimoto, all of Sodegaura, Japan

[73] Assignee: Idemitsu Kosan Company Limited, Tokyo, Japan

[21] Appl. No.: 26,496

[22] Filed: Mar. 4, 1993

[30] Foreign Application Priority Data

Mar. 19, 1992 [JP] Japan ................................. 4-063875

[51] Int. Cl.$^5$ ................................. C07C 2/62
[52] U.S. Cl. ................................. 585/709; 585/721
[58] Field of Search ................................. 585/721, 709

[56] References Cited

U.S. PATENT DOCUMENTS

| | | |
|---|---|---|
| 3,655,813 | 4/1972 | Kirsch et al. |
| 3,865,894 | 2/1975 | Kirsch et al. |
| 3,975,299 | 8/1976 | Crathorne et al. ............ 585/721 |
| 4,301,315 | 4/1981 | Haskell et al. ............ 585/709 |
| 4,761,504 | 8/1988 | Pujado ............ 585/331 |
| 5,095,167 | 3/1992 | Christensen. |

FOREIGN PATENT DOCUMENTS

| | | |
|---|---|---|
| 0440250A2 | 8/1991 | European Pat. Off. |
| 46-41223 | of 0000 | Japan. |
| 51-68501 | 6/1976 | Japan. |
| 61-183230 | 8/1986 | Japan. |

*Primary Examiner*—Asok Pal
*Attorney, Agent, or Firm*—Frishauf, Holtz, Goodman & Woodward

[57] ABSTRACT

A process for alkylating an isoparaffin comprising reacting an isoparaffin with a monoolefin in the presence of a salt of a heteropoly-acid as a solid catalyst. The salt of the heteropoly-acid is a compound obtained by substituting a cation for a hydrogen ion of a heteropoly-acid of the formula $H_k \cdot X \cdot Y_m \cdot Z_{12-m} \cdot O_{40} \cdot nH_2O$, wherein X is a hetero-atom selected from the group consisting of P, Si, Ge and As, each of Y and Z is a polyatom selected from the group consisting of W, Mo and V, k is 3 or 4, m is 0 or 1, and n is a positive number.

19 Claims, No Drawings

PROCESS FOR ALKYLATING AN ISOPARAFFIN WITH A SALT OF A HETEROPOLY-ACID AS A CATALYST

BACKGROUND OF THE INVENTION

1. Field of the Invention

The present invention relates to a process for alkylating an isoparaffin, which process is suitable for obtaining an alkylate gasoline used as a gasoline base having a high octane number.

2. Prior Art

It is the practice under the present situation to decrease the aromaticity of automobile gasoline, and there is required a gasoline base whose aromatic content is small and whose octane number is high. A process for producing alkylate gasoline from isoparaffin and olefin by alkylation is attracting attention.

In the process for producing alkylate gasoline by the above alkylation method, it is known to use, as a catalyst, a liquid catalyst such as sulfuric acid or hydrogen fluoride. It has been also proposed to use a solid catalyst such as crystalline aluminosilicate (JP-B-46-41223), modified zeolite (JP-A-51-68501) or an ultra-acidic zirconia catalyst (JP-A-61-183230).

In the above alkylation method using a liquid catalyst such as sulfuric acid or hydrogen fluoride, not only is it required to carry out a step of separating the reaction product and the liquid catalyst after the reaction, but also there are problems in corrosion of an apparatus and treatment of waste acid.

The alkylation method using the above solid catalyst is excellent by using a liquid catalyst, since it is free of the above problems involved in the method using a liquid catalyst, and since it has advantages of simple reaction operation and durability of an apparatus. However, for example, the alkylation method using an ultra-acidic zirconia catalyst has a disadvantage that the yield of alkylate gasoline is extremely low. It has been therefore desired to develop a novel solid catalyst for alkylation other than the above three solid catalysts for alkylation.

SUMMARY OF THE INVENTION

It is therefore an object of the present invention to provide a process for alkylating an isoparaffin, in which alkylate gasoline can be obtained at high yields in the presence of a novel solid catalyst for alkylation.

The present inventors have made a study to achieve the above object, and as a result, have found that alkylate gasoline can be obtained at high yields by using a salt of heteropoly-acid as a solid catalyst in the alkylation of an isoparaffin in which an isoparaffin is reacted with a monoolefin.

Therefore, the present invention has its gist in a process for alkylating an isoparaffin, which comprises reacting an isoparaffin with a monoolefin in the presence of a salt of a heteropoly-acid.

DETAILED DESCRIPTION OF THE INVENTION

The present invention will be detailed hereinafter.

The isoparaffin used as a starting material in the present invention preferably includes isoparaffins having 4 to 6 carbon atoms such as isobutane, isopentane and isohexane. The isoparaffin used for the reaction may be a single isoparaffin selected from isoparaffins having 4 to 6 carbon atoms, and it may be also a mixture of any two members of these isoparaffins. The isoparaffin may also contain a hydrocarbon other than the isoparaffin.

The monoolefin which is allowed to react with the above isoparaffin preferably includes monoolefins having 3 to 6 carbon atoms such as propylene, butene, pentene and hexene. The monoolefin used for the reaction may be a single monoolefin selected from monoolefins having 3 to 6 carbon atoms, and it may be a mixture of any two members of these monoolefins. The monoolefin may also contain a hydrocarbon other than the monoolefin.

In the present invention, the reaction between the above isoparaffin and monoolefin is carried out in the presence of a salt of a heteropoly-acid as a solid catalyst.

The salt of a heteropoly-acid is a compound obtained by substituting a cation for a hydrogen ion of a heteropoly-acid. Particularly preferred is a compound which is obtained by substituting a cation for a hydrogen ion of a heteropoly-acid of the formula (I),

$$H_k \cdot X \cdot Y_m \cdot Z_{12-m} \cdot O_{40} \cdot nH_2O \qquad (I)$$

(wherein

X is a hetero-atom selected from the group consisting of P, Si, Ge and As, each of Y and Z is a polyatom selected from the group consisting of W, Mo and V and may be the same as, or different from, other, k is a number (3 or 4) of hydrogen atoms, m is a number (0 or 1) of Y, and n is a positive number showing a hydration water number), and which is represented by the formula (II),

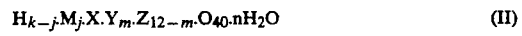

$$H_{k-j} \cdot M_j \cdot X \cdot Y_m \cdot Z_{12-m} \cdot O_{40} \cdot nH_2O \qquad (II)$$

wherein

M is a cation selected from the group consisting of alkali metal ion, alkaline earth metal ion, IIIB metal ion and ammonium ion, j is a number ($0 < j \leq k$) of M substituted for hydrogen in the heteropoly-acid of the formula (I), and X, Y, Z, k, m and n are as defined in the above formula (I).

Examples of the alkali metal ion as M in the formula (II) are Li, Na, K, Rb and Cs ions; examples of the alkaline earth metal ion are Be, Mg, Ca, Sr and Ba ions; and examples of the IIIB metal ion are Ga, In and Tl ions.

In the formula (II), j is a number which satisfies the relationship of $0 < j \leq k$. If $j = k$, the formula means a neutral salt of heteropoly-acid in which hydrogen atom of heteropoly-acid has been completely substituted by cation M. In case of $0 < j < k$, the formula means an acidic salt of heteropoly-acid in which hydrogen atom of heteropoly-acid has been partially substituted by cation M, i.e., the hydrogen atom is partially remaining therein.

Specific examples of the salt of a heteropoly-acid, represented by the above formula (II), are as follows.

$$H_{3-j}M_jPW_{12}O_{40} \qquad (1)$$

$$H_{4-j}M_jSiW_{12}O_{40} \qquad (2)$$

$$H_{3-j}M_jPMo_{12}O_{40} \qquad (3)$$

$$H_{4-j}M_jSiMo_{12}O_{40} \qquad (4)$$

  (5)

  (6)

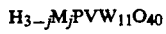  (7)

  (8)

In the above formulae (1) to (8), M is alkali metal ion, alkaline earth metal ion or ammonium ion. In the above formulae (1), (3) and (7), $0 < j \leq 3$, and in the above formulae (2), (4), (5), (6) and (8), $0 < j \leq 4$.

In the present invention, an isoparaffin is allowed to react with a monoolefin in the presence of a salt of heteropoly-acid. This reaction is preferably carried out through a fixed bed or a suspended bed.

In the reaction through a fixed bed, a reactor is packed with a salt of a heteropoly-acid as a catalyst, the reaction temperature is generally set between 0° to 200° C., preferably between 0° to 150° C., the reaction pressure is generally set between 0 and 50 kg/cm²G, preferably between 5 and 30 kg/cm²G, and the isoparaffin and the monoolefin are introduced to the reactor packed with the catalyst to allow these two members to react while the catalyst is fixed. The isoparaffin (IP)-/monoolefin (MO) molar ratio (IP/MO) is generally set at 1 to 100:1. The reasons therefor are as follows. When IP/MO is smaller than 1, monoolefin reacts with one another to increase the amount of byproducts. When IP/MO is larger than 100:1, the amount of unreacted paraffin is large, which is uneconomical. The IP/MO is particularly preferably 5 to 80.

The WHSV (space velocity) of olefin is set at 0.01 to 10 h$^{-1}$. The reasons therefor are as follows. When the WHSV is smaller than 0.01 h$^{-1}$, the productivity is poor. When the WHSV is larger than 10 h$^{-1}$, the contact efficiency of olefin and paraffin is poor. The WHSV is particularly preferably 0.05 to 5 h$^{-1}$.

In the reaction through a suspended bed, a reactor is packed with a salt of a heteropoly-acid as a catalyst, an isoparaffin and a monoolefin are introduced into the reactor packed with the catalyst while the isoparaffin and monoolefin are in a liquid state, and these two members are allowed to react while the catalyst is in a suspended state. The reaction temperature, reaction pressure and isoparaffin/monoolefin molar ratio (IP/MO) are the same as those specified regarding the above reaction through the fixed bed. In this reaction through the suspended bed, the amount of olefin per gram of the catalyst is 0.01 to 0.1 g. The reasons therefor are as follows. When the above amount is less than 0.01 g, the amount of the catalyst relative to the olefin is too large to stir the catalyst smoothly, which is uneconomical. When the above amount exceeds 0.1 g, the contact efficiency of the olefin and catalyst is poor, and the product yield is low. The amount of the olefin per gram of the catalyst is particularly preferably 0.03 to 0.08 g.

The present invention will be explained hereinafter by reference to Examples.

CATALYST PREPARATION EXAMPLE (i) About 25 g of 12-tungstophosphoric acid ($H_3PW_{12}O_{40}.nH_2O$) was dissolved in about 150 ml of pure water to prepare an $H_3PW_{12}O_{40}$ aqueous solution (hereinafter referred to as solution A). This solution A was titrated with a 0.1N NaOH aqueous solution to determine the exact amount of $H_3PW_{12}O_{40}$ in the solution A.

$Cs_2CO_3$ was used as a substance containing a cation substitutable for a hydrogen ion of $H_3PW_{12}O_{40}.nH_2O$, and measured for a water content by thermogravimetric analysis. Then, $Cs_2CO_3$ weighed out in such an amount that it would react with $H_3PW_{12}O_{40}.nH_2O$ to give $H_{0.5}Cs_{2.5}PW_{12}O_{40}.nH_2O$, and then it was dissolved in about 100 ml of pure water to prepare a $Cs_2CO_3$ aqueous solution (hereinafter referred to as solution B).

Then, the solution B was little by little added to the solution A with stirring, and the resultant mixture was evaporated to dryness to give $H_{0.5}Cs_{2.5}PW_{12}O_{40}.nH_2O$ (hereinafter referred to as $Cs_{2.5}$ salt).

(ii) $H_{0.7}Cs_{2.3}PW_{12}O_{40}.nH_2O$ (hereinafter referred to as $Cs_{2.3}$ salt) and $H_{0.3}Cs_{2.7}PW_{12}O_{40}.nH_2O$ ($Cs_{2.7}$ salt) were obtained in the same manner as in the above (i) except that the $Cs_2CO_3$ amount was changed.

(iii) $H_{0.5}Rb_{2.5}PW_{12}O_{40}.nH_2O$ (hereinafter referred to as $Rb_{2.5}$ salt), $H_{0.5}K_{2.5}PW_{12}O_{40}.nH_2O$ ($K_{2.5}$ salt), $H_{0.5}Tl_{2.5}PW_{12}O_{40}.nH_2O$ ($Tl_{2.5}$ salt) and $H_{0.5}(NH_4)_{2.5}PW_{12}O_{40}.nH_2O$ (($NH_4$)$_{2.5}$ salt) were obtained in the same manner as in the above (i) except that the $Cs_2CO_3$ was replaced with predetermined amounts of $Rb_2CO_3$, $K_2CO_3$, $TlNO_3$ and $NH_4NO_3$.

EXAMPLE 1

The $Cs_{2.5}$ salt obtained in (i) of Catalyst Preparation Example was molded to a size of 16 to 32 mesh, and 1.5 g of the molded $Cs_{2.5}$ salt was packed into a reactor. The $Cs_{2.5}$ salt in the reactor was dried in $N_2$ at 120° C., and preliminarily treated in $N_2$ at 300° C.

Then, isobutane and isobutene were introduced into the catalyst-packed reactor at a rate of 12 g/h (WHSV of olefin=0.16 h$^{-1}$) in such a manner that the isobutane/isobutene molar ratio was 50/1 at a reaction temperature of 50° C. at a total pressure of 25 kg/cm²G, and these two members were allowed to react through the fixed bed. Table 1 shows the yield of a reaction product obtained 0.4 hour after the reaction was initiated. Table 1 clearly shows that trimethylpentane (isooctane) as an intended reaction product can be obtained at a high yield.

EXAMPLES 2, 3, 4 AND 5

Example 1 was repeated except that the $Cs_{2.5}$ salt was replaced with the $Rb_{2.5}$ salt (Example 2), $K_{2.5}$ salt (Example 3), $Tl_{2.5}$ salt (Example 4) and ($NH_4$)$_{2.5}$ salt (Example 5) to give trimethylpentane at high yields as shown in Table 1.

EXAMPLES 6, 7 AND 8

Example 1 was repeated using the $Cs_{2.7}$ salt (Example 6), $Cs_{2.5}$ salt (Example 7) and $Cs_{2.3}$ salt (Example 8) except that the reaction temperature was changed to 100° C., to give trimethylpentane at high yields as shown in Table 1.

EXAMPLE 9

Example 1 was repeated using the $Cs_{2.5}$ salt except that the reaction temperature was changed to 20° C. to give trimethylpentane at a high yield as shown in Table 1.

REFERENTIAL EXAMPLE

Example 1 was repeated except that 12-tungstophosphoric acid ($H_3PW_{12}O_{40}.nH_2O$) was used and that the reaction temperature was changed to 100° C. As shown in Table 1, however, no trimethylpentane was formed.

COMPARATIVE EXAMPLE 1

Example 1 was repeated except for the use of an ultra-strong acidic zirconia catalyst prepared according to the Example in JP-A-61-183230. As shown in Table 1, however, the yield of trimethylpentane as an objective product was 11%, or extremely lower than any yield in Examples 1 to 9.

TABLE 1

|  | Catalyst | Reaction temperature (°C.) | Yields of Products (%)[2] | | | | |
|---|---|---|---|---|---|---|---|
|  |  |  | $C_5-C_7$[3] | TMP[4] | Other $C_8$ component[5] | $C_9+$[6] | $C_5+$[7] |
| Ex. 1 | $Cs_{2.5}$ salt | 50 | 41 | 98 | 4 | 25 | 163 |
| Ex. 2 | $Rb_{2.5}$ salt | 50 | 58 | 109 | 7 | 14 | 188 |
| Ex. 3 | $K_{2.5}$ salt | 50 | 53 | 127 | 7 | 10 | 197 |
| Ex. 4 | $Tl_{2.5}$ salt | 50 | 64 | 106 | 7 | 18 | 195 |
| Ex. 5 | $(NH_4)_{2.5}$ salt | 50 | 64 | 115 | 8 | 12 | 199 |
| Ex. 6 | $Cs_{2.7}$ salt | 100 | 21 | 36 | 8 | 65 | 130 |
| Ex. 7 | $Cs_{2.5}$ salt | 100 | 56 | 59 | 21 | 13 | 149 |
| Ex. 8 | $Cs_{2.3}$ salt | 100 | 108 | 50 | 29 | 9 | 196 |
| Ex. 9 | $Cs_{2.5}$ salt | 20 | 28 | 73 | 2 | 58 | 161 |
| REx. | HPW[1] | 100 | 0 | 0 | 23 | 112 | 135 |
| CEx. 1 | Ultra-strong acidic zirconia | 20 | 9 | 11 | 1 | 81 | 102 |

Ex. = Example, REx. = Referential Example, CEx. = Comparative Example
[1]HPW: $H_3PW_{12}O_{40} \cdot nH_2O$
[2]Weight % of product based on isobutene as raw material.
[3]$C_5-C_7$: Products having 5 to 7 carbon atoms.
[4]TMP: Trimethylpentane (isooctane) as an intended product.
[5]Other $C_8$ component: $C_8$ product other than TMP.
[6]$C_9+$: Products having at least 9 carbon atoms.
[7]$C_5+$: Total amount of products having at least 5 carbon atoms.

As explained above, according to the present invention, there can be obtained higher isoparaffin at high yields by using a salt of a heteropoly-acid in the reaction between an isoparaffin and a monoolefin. The present invention is useful for producing alkylate gasoline as a gasoline base having a high octane number.

What is claimed is:

1. A process for alkylating an isoparaffin, which comprises reacting an isoparaffin with a monoolefin in the presence of a salt of a heteropoly-acid.

2. The process according to claim 1, wherein the salt of the heteropoly-acid is a compound which is obtained by substituting a cation for a hydrogen ion of a heteropoly-acid of the formula (I), $$H_k \cdot X \cdot Y_m \cdot Z_{12-m} \cdot O_{40} \cdot nH_2O \quad (I)$$

wherein
X is a hetero-atom selected from the group consisting of P, Si, Ge and As,
each of Y and Z is a polyatom selected from the group consisting of W, Mo and V and are the same as, or different from each other,
k is 3 or 4,
m is 0 or 1, and
n is a positive number representing a hydration water number,
said salt being represented by the formula (II), $$H_{k-j} M_j \cdot X \cdot Y_m \cdot Z_{12-m} \cdot O_{40} \cdot nH_2O \quad (II)$$

wherein
M is a cation selected from the group consisting of an alkali metal ion, an alkaline earth metal ion, a IIIB metal ion and an ammonium ion,
j is a number defined by the following relationship: $0 < j \leq k$, and
X, Y, Z, k, m and n are as defined for said formula (I).

3. The process according to claim 2, wherein M is at least one alkali metal ion selected from the group consisting of Li, Na, K, Rb and Cs ions.

4. The process according to claim 2, wherein M is at least one alkaline earth metal ion selected from the group consisting of Be, Mg, Ca, Sr and Ba ions.

5. The process according to claim 2, wherein M is at least one IIIB metal ion selected from the group consisting of Ca, In and Tl ions.

6. The process according to claim 2, wherein the salt of the heteropoly-acid is at least one member selected from the group consisting of:

$$H_{3-j} M_j PW_{12}O_{40} \quad (1)$$

$$H_{4-j} M_j SiW_{12}O_{40} \quad (2)$$

$$H_{3-j} M_j PMo_{12}O_{40} \quad (3)$$

$$H_{4-j} M_j SiMo_{12}O_{40} \quad (4)$$

$$H_{4-j} M_j GeW_{12}O_{40} \quad (5)$$

$$H_{4-j} M_j GeMo_{12}O_{40} \quad (6)$$

$$H_{3-j} M_j PVW_{11}O_{40}, \text{ and} \quad (7)$$

$$H_{4-j} M_j SiVMo_{11}O_{40} \quad (8)$$

in which M is a cation selected from the group consisting of an alkali metal ion, an alkaline earth metal ion, a IIIB metal ion and an ammonium ion, and j is defined by the following relationships: $0 < j \leq 3$ in the above formula (1), (3) and (7), and $0 < j \leq 4$ in the above formulae (2), (4), (5), (6) and (8).

7. The process according to claim 1, wherein the isoparaffin is $C_4-C_6$ isoparaffin.

8. The process according to claim 1, wherein the monoolefin is $C_3-C_6$ monoolefin.

9. The process according to claim 1, wherein the reaction is carried out in a fixed bed or a suspended bed.

10. The process according to claim 9, wherein the reaction in the fixed bed or the suspended bed is carried out at a temperature of 0° to 200° C.

11. A process according to claim 9, wherein the reaction through the fixed bed or the suspended bed is carried out under pressure of 0 to 50 kg/cm²G.

12. The process according to claim 9, wherein the reaction in the fixed bed or the suspended bed is carried out with an isoparaffin/monoolefin molar ratio of 1 to 100:1.

13. The process according to claim 9, wherein the reaction is carried out in a fixed bed with a WHSV of the monoolefin of 0.01 to 10 $h^{-1}$.

14. The process according to claim 9, wherein the reaction is carried out in a suspended bed with an monoolefin/catalyst weight ratio being such that the monoolefin is in an amount of 0.01 to 0.1 g per gram of the catalyst.

15. The process according to claim 10, wherein the temperature is 0° to 150° C. and the reaction is carried out at a pressure of 5 to 30 kg/cm$^2$G and at a WHSV of 0.05 to 5 $h^{-1}$.

16. The process according to claim 14, wherein monoolefin is in an amount of 0.03 to 0.08 g per gram of the catalyst.

17. The process according to claim 7, wherein the monoolefin is a $C_3$–$C_6$ monoolefin; the isoparaffin/monoolefin molar ratio is 1 to 100:1; and the process is carried out in a fixed bed or a suspended bed at a temperature of 0° to 200° C. and at a pressure of 0 to 50 kg/cm$^2$G.

18. The process according to claim 2, wherein the salt of a heteropoly-acid is selected from the group consisting of $H_{0.7}Cs_{2.3}PW_{12}O_{40} \cdot nH_2O$, $H_{0.3}Cs_{2.7}PW_{12}O_{40} \cdot nH_2O$, $H_{0.5}Rb_{2.5}PW_{12}O_{40} \cdot nH_2O$, $H_{0.5}K_{2.5}PW_{12}O_{40} \cdot nH_2O$, $H_{0.5}Cs_{2.5}PW_{12}O_{40} \cdot nH_2O$, $H_{0.5}Tl_{2.5}PW_{12}O_{40} \cdot nH_2O$, and $H_{0.5}(NH_4)_{2.5}PW_{12}O_{40} \cdot nH_2O$.

19. The process according to claim 17, wherein the salt of a heteropoly-acid is selected from the group consisting of $H_{0.7}Cs_{2.3}PW_{12}O_{40} \cdot nH_2O$, $H_{0.3}Cs_{2.7}PW_{12}O_{40} \cdot nH_2O$, $H_{0.5}Rb_{2.5}PW_{12}O_{40} \cdot nH_2O$, $H_{0.5}K_{2.5}PW_{12}O_{40} \cdot nH_2O$, $H_{0.5}Cs_{2.5}PW_{12}O_{40} \cdot nH_2O$, $H_{0.5}Tl_{2.5}PW_{12}O_{40} \cdot nH_2O$, and $H_{0.5}(NH_4)_{2.5}PW_{12}O_{40} \cdot nH_2O$.

* * * * *